US00PP13252P3

(12) United States Plant Patent
Utecht

(10) Patent No.: US PP13,252 P3
(45) Date of Patent: Nov. 19, 2002

(54) GERANIUM PLANT NAMED 'FISROMAG'

(75) Inventor: Angelika Utecht, Montabaur (DE)

(73) Assignee: Florfis AG, Binningen (CH)

( * ) Notice: Subject to any disclaimer, the term of this patent is extended or adjusted under 35 U.S.C. 154(b) by 0 days.

(21) Appl. No.: 09/991,976

(22) Filed: Nov. 26, 2001

(65) Prior Publication Data

US 2002/0088042 P1 Jul. 4, 2002

(51) Int. Cl.[7] ..... A01H 5/00

(52) U.S. Cl. ..... Plt./329

(58) Field of Search ..... Plt./329

*Primary Examiner*—Kent L. Bell
(74) *Attorney, Agent, or Firm*—Foley & Lardner

(57) ABSTRACT

A new and distinct cultivar of geranium plant named 'Fisromag', as described and illustrated, and particularly characterized by the combined features of red-purple semi-double flowers, medium size inflorescences, medium green foliage with weak zonation, and relatively compact, low medium sized.

1 Drawing Sheet

BOTANICAL CLASSIFICATION

*Pelargonium zonale.*

VARIETY DENOMINATION

'Fisromag'.

BACKGROUND OF THE INVENTION

The present invention comprises a new and distinct cultivar of geranium, botanically known as *Pelargonium zonale*, and hereinafter referred to by the cultivar name 'Fisromag'.

'Fisromag' is a product of a planned breeding program which had the objective of creating new geranium varieties with magenta to purple flower color, medium green foliage in combination with medium to tall plant habit.

'Fisromag' originated from a hybridization made by the inventor, Angelika Utecht in a controlled breeding program in Galdar, Gran Canaria, Spain, in 1996. The female parent was a hybrid seedling, No. K94-1960-1, having purple-pink, single-type flowers, large inflorescences, dark-green foliage, with only very weak zonation, and medium sized, but somewhat open and irregular plant habit. The male parent of 'Fisromag' was the patented variety 'HWD Violetta' (U.S. Plant Pat. No. 9,748) which is characterized by red-purple, semi-double flowers, medium green foliage with slight zonation, and medium sized plant habit.

'Fisromag' was selected as one flowering plant within the progeny of the stated cross by Angelika Utecht in 1997 in a controlled environment in Galdar, Gran Canaria, Spain. The first act of asexual reproduction of 'Fisromag' was accomplished when vegetative cuttings were taken from the initial selection in the fall of 1997, in a controlled environment in Galdar, Gran Canaria, Spain, by, or under the supervision of, Angelika Utecht.

Horticultural examination of plants grown from cuttings of the plant initiated in May 1998, in Hillscheid, Federal Republic of Germany, and continuing thereafter, has demonstrated that the combination of characteristics as herein disclosed for 'Fisromag' are firmly fixed and are retained through successive generations of asexual reproduction. The new cultivar reproduces true to type.

'Fisromag' has not been observed under all possible environmental conditions. The phenotype may vary significantly with variations in environment such as temperature, light intensity and day length. The following observations, measurements, and comparisons describe plants grown in Hillscheid, Germany, and in Langley, British Columbia, Canada, under greenhouse conditions which approximate those generally used in commercial practice.

BRIEF DESCRIPTION OF THE INVENTION

The following traits have been repeatedly observed and are determined to be basic characteristics of 'Fisromag' in combination distinguish this geranium as a new and distinct cultivar:

1. Round, red-purple colored flowers;
2. Medium sized, semi-spherically shaped inflorescences;
3. Medium green, relatively large leaves with weak zonation;
4. Moderately compact growth, medium sized, but relatively low plant habit; and
5. Mid season spring flowering response.

Of the many commercial cultivars known to the present inventor, the most similar in comparison to 'Fisromag' are the varieties 'Fisdino' (U.S. Plant Pat. No. 8,761), 'Fispurple' (U.S. Plant Pat. No. 12,368), the parental cultivar 'HWD Violetta', and the related, cultivar 'Fisroyal', U.S. Plant patent application Ser. No. 09/991,636. In comparison to 'Fisdino', 'Fisromag' has slightly less bluish hue of general flower color, more round shaped flowers, less distinct markings on petals, and generally much more compact plant habit.

In contrast to 'Fispurple', 'Fisromag' has small red macules on upper petals, and is not early flowering, but in the medium range. Furthermore, 'Fisromag' has larger leaves, and somewhat more vigorous growth.

In comparison to 'HWD Violetta', 'Fisromag' has small red eyes on upper petals, which lack with 'HWD Violetta', and somewhat less compact plant habit.

In comparison to 'Fisroyal', 'Fisromag' has a more bluish shade of flower color, somewhat less distinct markings on petals, but somewhat stronger zonation on leaves, and somewhat more compact and lower plant habit.

BRIEF DESCRIPTION OF THE DRAWING

The accompanying photographic drawing shows typical flower and foliage characteristics of 'Fisromag' with colors being as true as possible with an illustration of this type.

The drawing shows a flowering pot plant in 14 cm container.

DETAILED BOTANICAL DESCRIPTION

The measurements were taken in Langley in early July, 2001, 18 weeks after planting of rooted cuttings. The plants were growing in 8 inch containers, they had not been pinched. In the following description color references are made to The Royal Horticultural Society Colour Chart (R.H.S.). The color values were determined indoors from flowering plants growing in greenhouse in May 2001, in Hillscheid, Germany.

Inflorescence:
- *Type.*—Umbel.
- *Shape.*—Semi-spherical.
- *Average diameter.*—122 mm.
- *Average depth.*—65 mm.
- *Peduncle length.*—188 mm.
- *Peduncle color.*—Light green, RHS 144 A, no anthocyanin.
- *Pedicle.*—Length 25.6 mm.
- *Pedicel color.*—Base light green, RHS 144 B, main part brownish, from RHS 179 A to 184 A.
- *Number of flowers per umbel.*—About 25.

Corolla:
- *Average diameter.*—47 mm.
- *Form.*—Semi-double.
- *Shape.*—Round, cup-shaped.
- *Number of petals.*—7.0.
- *Number of petaloids.*—1–2, narrow, same color as the petals.
- *Shape of petals.*—Obovate, base attenuate, upper end margin is mainly entire at apex slight serrulation may occur.
- *Size of petals.*—Upper petals: length 24–26 mm; width 20–22 mm. Lower petals: length 23–25 mm; width 23–25 mm.
- *Color* (*general tonality from a distance of three meters*). —Magenta/bluish red.
- *Color of upper petals.*—Between RHS 57 A and 57 B.
- *Markings of upper petals.*—Weak red macules, RHS 46B, and salmon-pink base, about RHS 47 C.
- *Color of lower petals.*—RHS 57 B.
- *Markings of lower petals.*—Very small dots, almost invisible, purple-red, RHS 57 A.
- *Color of lower surface of petals.*—Upper petals RHS 52 A, lower petals RHS 57 C.
- *Color of sepals.*—Outer surface light green, RHS 143 B, near base RHS 184 A; inner surface light green, RHS 143 C, near base RHS 181 A.
- *Number of sepals.*—5.
- *Shape of sepals.*—Linear to lanceolate, acute tip, truncate base, surface with very short pubescence, margin entire.
- *Size of sepals.*—10–11 mm long, 4 mm wide for the largest upper sepal, 3 mm in width for the other sepals.

Bud: (just before petals unfold):
- *Shape.*—Elliptical.
- *Color* (*sepals*).—Light green, RHS 143 A.
- *Color* (*petals*).—Bluish-red, RHS 57 A.
- *Length.*—17 mm.
- *Width.*—10 mm.

Reproductive organs:
- *Androecium.*—About 5 fertile anthers, filaments white, RHS 155 D, to light pink, RHS 66 D, moderate pollen, orange, RHS 30 A.
- *Gynoecium.*—One pistil, style and stigma purple-red, RHS 66 B, 5 to 6 lobed stigma.
- *Fertility/seed set.*—Occasionally a few seeds are developed, Fruit: Oblong, about 5–6 mm in diameter, with rostrum (beak), total length about 38–40 mm. Seed: Oblong, 4–5 mm long, brown, RHS 177 B.

Spring flowering resonse period: In Hillscheid, Germany, in 2000 plants had on average 0.9 flowers opened 8 weeks after planting of rooted cuttings.

Outdoor flower production: Continuously flowering, the flower count in 2000. in Hillscheid, Germany, indicated about 1.6 inflorescence per plant in mid May.

Durability: Good stability of flower color relatively good rain resistance.

Lastingness of the individual flower: About 8–9 days at 18° C., about 18 days for the umbel.

Pest/disease resistance/susceptibility: No observations to date.

Fragrance: None.

PLANT

Foliage:
- *Shape.*—Kidney-shaped, with open, cordate base, and relatively distinct lobes.
- *Margin.*—Bicrenated, distinctly wavy.
- *Texture.*—Upper surface smooth, velvety.
- *Size of leaf.*—84 mm wide, 52 mm long.
- *Color of upper surface.*—Medium green, approximately RHS 137 C.
- *Color of zonation.*—Brown, about RHS 166 A.
- *Color of lower surface.*—RHS 137 D.
- *Petioles.*—40–50 mm long, 3 mm diameter, light green in color, approximately RHS 144 A.

General appearance and form:
- *Stem color.*—Light green, RHS 144 B.
- *Internode length.*—About 10 mm.
- *Branching pattern.*—Average 6.4 branches.
- *Size of plants.*—Height 30.2 cm, width 45.2 cm, as measured from the top of the soil (base of the main stem) to the surface of the foliage canopy, without inflorescences.

I claim:

1. A new and distinct cultivar of geranium plant named 'Fisromag', as described and illustrated herein.

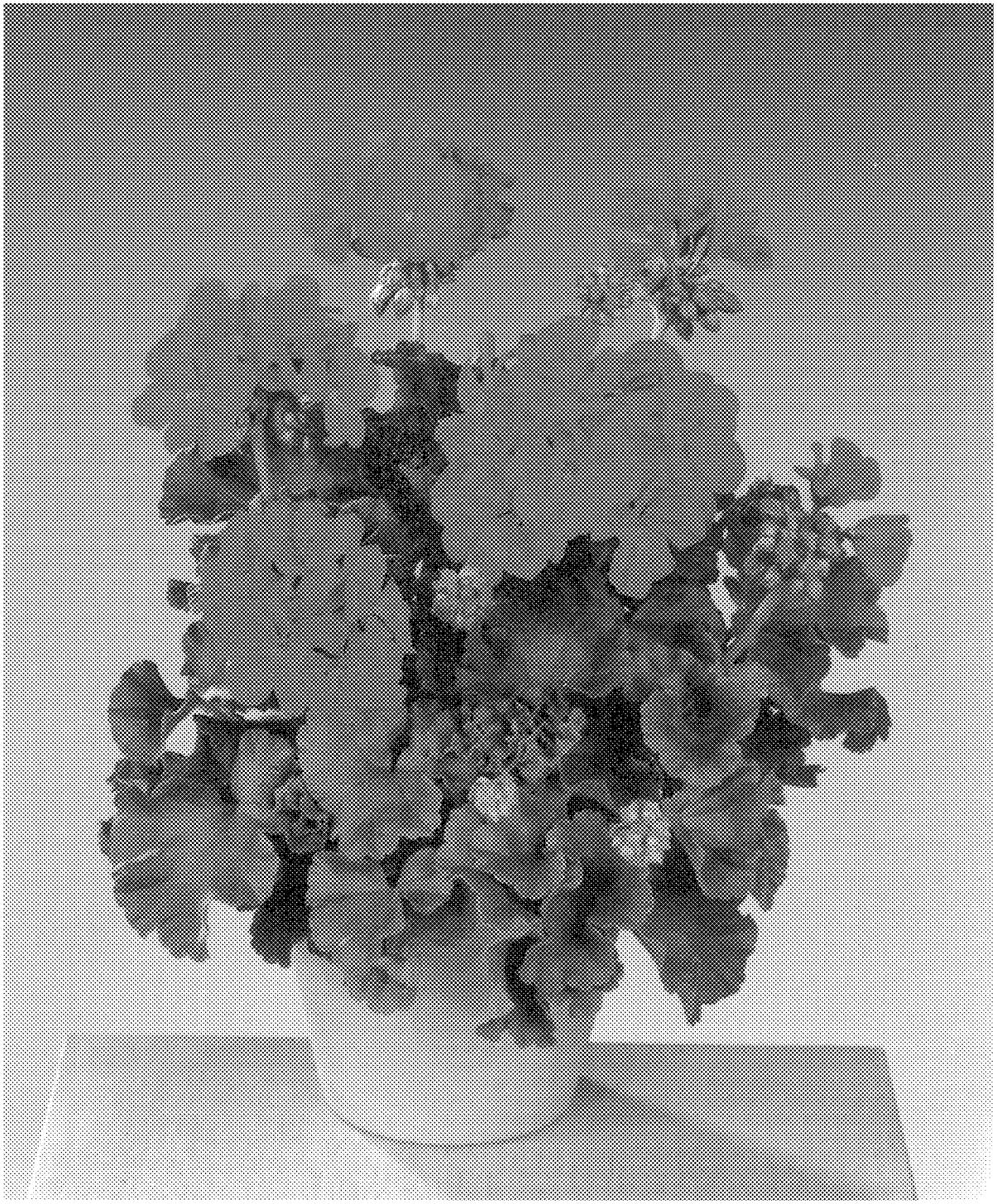

* * * * *